United States Patent
Fu et al.

(10) Patent No.: US 12,285,630 B2
(45) Date of Patent: Apr. 29, 2025

(54) SYSTEMS AND METHODS FOR CONTROLLING ELECTRON BEAM IN RADIOTHERAPY

(71) Applicant: SHANGHAI UNITED IMAGING HEALTHCARE CO., LTD., Shanghai (CN)

(72) Inventors: Feichao Fu, Shanghai (CN); Peng Wang, Shanghai (CN); Shoubo He, Shanghai (CN); Peng Cheng, Shanghai (CN); Cheng Ni, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 273 days.

(21) Appl. No.: 17/820,555

(22) Filed: Aug. 17, 2022

(65) Prior Publication Data
US 2022/0387823 A1 Dec. 8, 2022

Related U.S. Application Data

(63) Continuation of application No. PCT/CN2020/085312, filed on Apr. 17, 2020.

(51) Int. Cl.
*A61N 5/10* (2006.01)
*G21K 1/00* (2006.01)

(52) U.S. Cl.
CPC ......... *A61N 5/1043* (2013.01); *A61N 5/1048* (2013.01); *A61N 5/1081* (2013.01); *G21K 1/003* (2013.01); *A61N 2005/1089* (2013.01)

(58) Field of Classification Search
CPC .. A61N 5/1043; A61N 5/1048; A61N 5/1081; A61N 2005/1089; A61N 5/1084; G21K 1/003; G21K 1/093
See application file for complete search history.

(56) References Cited

U.S. PATENT DOCUMENTS

| | | | |
|---|---|---|---|
| 4,987,309 A | 1/1991 | Klasen et al. | |
| 6,878,951 B2 | 4/2005 | Ma | |
| 8,614,429 B2 | 12/2013 | Balakin | |
| 9,711,253 B2 | 7/2017 | Alezra et al. | |

(Continued)

FOREIGN PATENT DOCUMENTS

| CN | 100998497 A | 7/2007 |
|---|---|---|
| CN | 101120871 A | 2/2008 |

(Continued)

OTHER PUBLICATIONS

Translation of CN205516039U (Year: 2016).*

(Continued)

*Primary Examiner* — Dani Fox
*Assistant Examiner* — Mamadou Faye
(74) *Attorney, Agent, or Firm* — METIS IP LLC

(57) ABSTRACT

According to an aspect of the present disclosure, a beam control device for radiotherapy is provided. The beam control device may include an electron beam generator configured to emit an electron beam for radiotherapy toward a subject in a first direction. The beam control device may further include a first deflection device configured to generate a defocused electron beam by defocusing the electron beam in a second direction, the second direction being different from the first direction.

20 Claims, 9 Drawing Sheets

(56) References Cited

U.S. PATENT DOCUMENTS

| | | | |
|---|---|---|---|
| 2012/0205555 A1 | | 8/2012 | Dirauf et al. |
| 2015/0270095 A1 | | 9/2015 | Kruit |
| 2017/0368373 A1 | * | 12/2017 | Sahadevan ............ A61N 5/1067 |
| 2019/0217125 A1 | * | 7/2019 | Bartkoski .......... A61N 1/37223 |

FOREIGN PATENT DOCUMENTS

| | | | | |
|---|---|---|---|---|
| CN | 103096611 | A | | 5/2013 |
| CN | 104941077 | A | | 9/2015 |
| CN | 205516039 | U | * | 8/2016 |
| CN | 107789749 | A | | 3/2018 |
| GB | 1157072 | | | 7/1969 |
| JP | S62285479 | A | | 12/1987 |

OTHER PUBLICATIONS

Emil Schüler et al., Very High-Energy Electron (VHEE) Beams in Radiation Therapy; Treatment Plan Comparison Between VHEE, VMAT, and PPBS, Medical Physics, 44(6): 2544-2555, 2017.

K. Kokurewicz et al., Focused Very High-Energy Electron Beams as A Novel Radiotherapy Modality for Producing High-Dose Volumetric Elements, Scientific Reports, 2019, 10 pages.

Y. Han et al., Optics Design and Beam Dynamics Simulation for A VHEE Radiobiology Beam Line at PRAE Accelerator, 10th International Particle Accelerator Conference, THPMP002: 3444-3447, 2019.

A. Lagzda et al., Relative Insensitivity to Inhomogeneities on Very High Energy Electron Dose Distributions, 8th International Particle Accelerator Conference, THPVA139: 4791-4794, 2017.

International Search Report in PCT/CN2020/085312 mailed on Jan. 15, 2021, 5 pages.

Written Opinion in PCT/CN2020/085312 mailed on Jan. 15, 2021, 4 pages.

The Extended European Search Report in European Application No. 20930974.9 mailed on Dec. 20, 2022, 6 pages.

\* cited by examiner

SYSTEMS AND METHODS FOR CONTROLLING ELECTRON BEAM IN RADIOTHERAPY

CROSS-REFERENCE TO RELATED APPLICATIONS

This application is a continuation of International Application PCT/CN2020/085312, filed on Apr. 17, 2020, the contents of which are hereby incorporated by reference.

TECHNICAL FIELD

The present disclosure generally relates to systems and methods for radiotherapy (RT), and more particularly, to systems and methods for controlling an electron beam in radiotherapy.

BACKGROUND

Radiotherapy is a widely used tool for cancer treatment in which a radiation beam may be delivered to a target area (e.g., a tumor) of a subject (e.g., a patient). The aim of radiotherapy is to deliver a maximum radiation dose to the target area while imposing a tolerable impact on a non-target area (e.g., a healthy organ or tissue around the target area). The radiation beam used in radiotherapy may include various types including, for example, an X-ray beam, an electron beam, a hadron beam, or the like, or any combination thereof. An X-ray beam may have a strong penetrating ability and usually be used to treat tumors inside the subject. However, the X-ray beam may deposit energy along its transmission path and cause damage to the non-target area. A hadron beam may include protons and/or ions, which may deposit the majority of their energy at a single point, i.e., a Bragg peak. The Bragg peak characteristic of the hadron beam may be exploited to achieve a desirable depth dose distribution. However, a hadron radiotherapy device may have a complicated structure, a high cost, and a slow energy switching speed.

With the development of electron acceleration techniques, electron beams with different energy levels have been used in radiotherapy. For example, an electron beam with a low energy level (e.g., an energy lower than 50 megaelectron volts (MeV)) may have a relatively insufficient penetrating ability and be used to treat tumors near the body surface of the subject. An electron beam with a high energy level (e.g., an energy higher than 50 MeV) may have a strong penetrability and a higher dose rate than the X-ray beam. It is desirable to develop systems and methods for controlling an electron beam, thereby providing an improved electron beam radiotherapy technique. For example, the improved electron beam radiotherapy technique may achieve a higher dose rate and an improved depth dose distribution than the X-ray radiotherapy technique, and/or a simpler system structure and a lower cost than the hadron radiotherapy technique.

SUMMARY

According to an aspect of the present disclosure, a beam control device for radiotherapy is provided. The beam control device may include an electron beam generator configured to emit an electron beam for radiotherapy toward a subject in a first direction. The beam control device may further include a first deflection device configured to generate a defocused electron beam by defocusing the electron beam in a second direction, the second direction being different from the first direction.

In some embodiments, an energy of the electron beam may be in a range from 50 megaelectron volts (MeV) to 300 MeV.

In some embodiments, the electron beam generator may be mounted on a gantry, and the second direction may be parallel to a rotation axis of the gantry.

In some embodiments, the beam control device may further include a second deflection device configured to generate a focused electron beam by focusing the defocused electron beam.

In some embodiments, the first deflection device may include a first microwave cavity.

In some embodiments, the second deflection device may include a second microwave cavity.

In some embodiments, the beam control device may further include a defocusing component configured to generate a second defocused electron beam by defocusing the focused electron beam in a third direction, the third direction being different from each of the first direction and the second direction. The beam control device may also include a focusing component configured to generate a second focused electron beam by focusing the second defocused electron beam in the third direction.

In some embodiments, the electron beam generator may be mounted on a gantry, and the third direction may be a horizontal direction perpendicular to a rotation axis of the gantry.

In some embodiments, at least one of the defocusing component or the focusing component may include at least one of a microwave cavity, a magnet, or a magnetic lens.

In some embodiments, the beam control device may further include a control device configured to control the first microwave cavity and the second microwave cavity such that the focused electron beam is focused on a target area of the subject in the second direction.

In some embodiments, to control the first microwave cavity and the second microwave cavity, the control device may be configured to determine one or more parameters of the first microwave cavity and the second microwave cavity based on at least one of a planned dose distribution, a position of the electron beam generator relative to the target area, a position of the first microwave cavity relative to the target area, or a position of the second microwave cavity relative to the target area.

In some embodiments, the beam control device may further include a scanning electrode configured to scan the defocused electron beam in a fourth direction, the fourth direction being different from each of the first direction and the second direction.

In some embodiments, the beam control device may further include a beam profile modulator. The beam profile modulator may be placed between the electron beam generator and the first microwave cavity and configured to shape the electron beam generated by the electron beam generator. The first microwave cavity may be configured to defocus the shaped electron beam.

In some embodiments, the beam profile modulator may include at least one of a multi-leaf collimator or a blocker.

In some embodiments, the beam control device may further include a second beam profile modulator configured to shape the defocused electron beam, wherein the first microwave cavity may be placed between the electron beam generator and the second beam profile modulator.

In some embodiments, the second beam profile modulator may include at least one of a multi-leaf collimator or a blocker.

In some embodiments, the first microwave cavity may be configured to defocus the electron beam in the second direction by applying a microwave field to the electron beam, the microwave field changing over time.

In some embodiments, the electron beam may include a plurality of micro-bunches sequentially generated by the electron beam generator with a time interval between each pair of consecutive micro-bunches of the plurality of micro-bunches. The microwave field may change at a periodicity, and the periodicity of the microwave field may be longer than the time interval.

According to another aspect of the present disclosure, a radiation delivery device may include a plurality of treatment heads each of which comprises a beam control device.

In some embodiments, the second direction may be perpendicular to a plane where the plurality of treatment heads are located.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
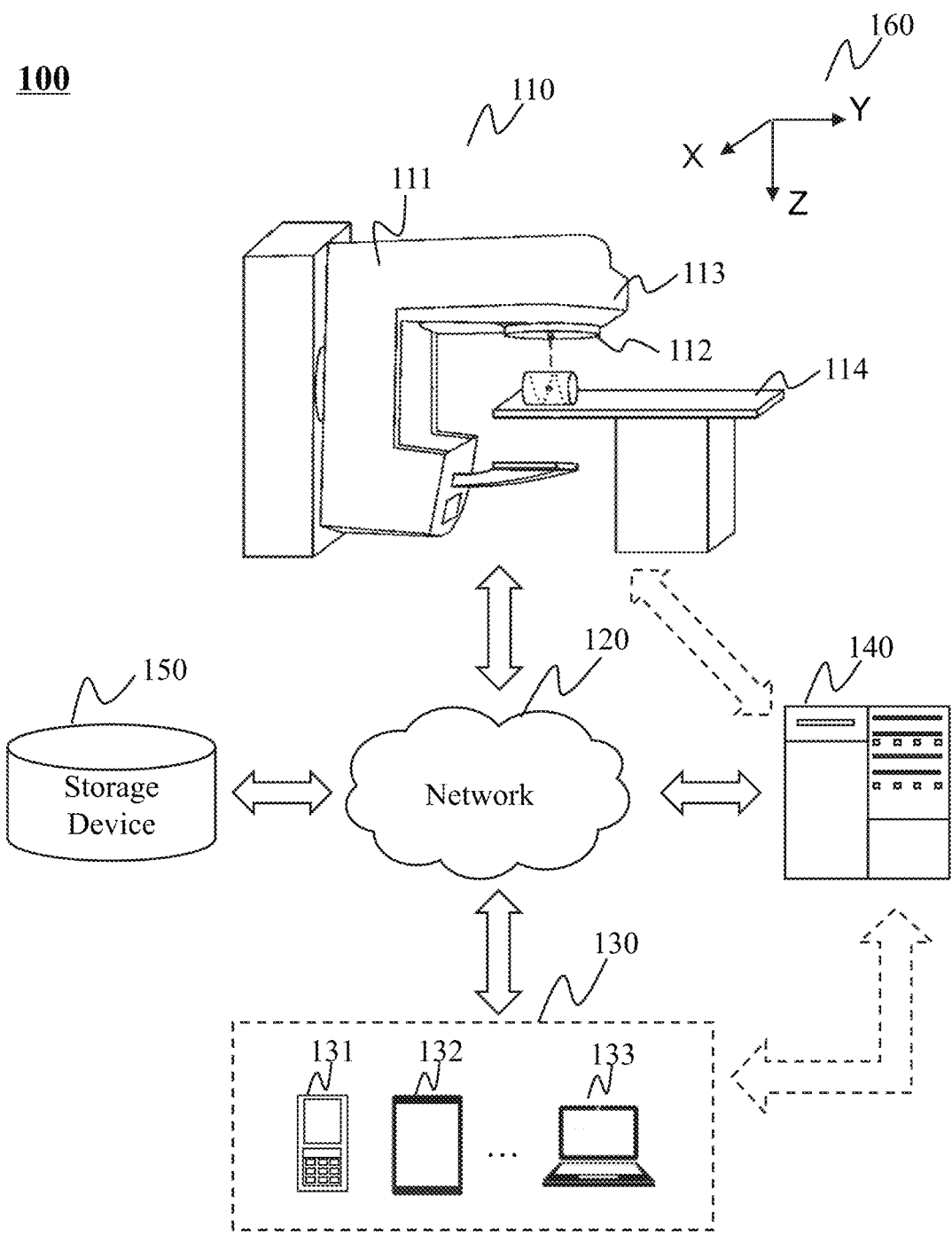
FIG. 1 is a schematic diagram illustrating an exemplary RT system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/ blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention.

Spatial and functional relationships between elements (for example, between layers) are described using various terms, including "connected," "engaged," "interfaced," and "coupled." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging and/or treatment, such as for disease diagnosis, treatment or research purposes. In some embodiments, the systems may include an RT system, a computed tomography (CT) system, an emission computed tomography (ECT) system, an X-ray photography system, a positron emission tomography (PET) system, or the like, or any combination thereof. For illustration purposes, the disclosure describes systems and methods for radiation therapy.

An aspect of the present disclosure relates to systems and methods for controlling an electron beam in radiotherapy. The systems may include an electron beam generator and a first microwave cavity. The electron beam generator may be configured to emit an electron beam for radiotherapy toward a subject in a first direction. The first microwave cavity may be configured to generate a defocused electron beam by defocusing the electron beam in a second direction. The second direction may be different from the first direction. Optionally, the systems may further include a second microwave cavity configured to generate a focused electron beam by focusing the defocused electron beam.

According to some embodiments of the present disclosure, the electron beam may be defocused and focused in a certain direction (e.g., the second direction) before entering the subject. The focused electron beam may be focused on a target area of the subject, thereby depositing more radiation dose on the target area and forming a "Bragg peak" like a hadron beam. Before reaching the target area, the focused electron beam may have a greater irradiation area in the subject, while the original electron beam may have a relatively small irradiation area if it is not defocused and focused. In other words, the radiation dose of the defocused electron beam may be scattered in the non-target area (e.g., the body surface and/or health organs between the body surface and the target area of the subject) more widely than the original electron beam, which may avoid or reduce a dose deposition in the non-target area. In this way, a desired depth dose distribution may be achieved, thereby improving the precision of treatment delivery, and/or reducing or avoiding damages to the subject caused by unintended radiation.

In addition, the deflection of the electron beam may be implemented by a microwave cavity. Compared with a deflection device (e.g., a magnet or a magnetic lens) that provides a constant deflection force, a microwave cavity may provide a dynamic microwave field. Moreover, the microwave field of a microwave cavity may have a higher field gradient than a magnetic field of a magnet. If the microwave field applies a same force on electrons as the magnetic field, it may achieve a better defocusing and/or focusing effect on electrons than the magnet field. In addition, the microwave cavity may have a smaller size than a deflection device that includes a magnet or a magnetic lens, which may reduce the equipment size and improve the equipment flexibility.

FIG. 1 is a schematic diagram illustrating an exemplary RT system 100 according to some embodiments of the present disclosure. As illustrated in FIG. 1, the RT system 100 may include a radiation delivery device 110, a network 120, one or more terminals 130, a processing device 140, and a storage device 150. In some embodiments, two or more components of the RT system 100 may be connected to and/or communicate with each other via a wireless connection (e.g., the network 120), a wired connection, or a combination thereof. The connection between the components of the RT system 100 may be variable. Merely by way of example, the radiation delivery device 110 may be connected to the processing device 140 through the network 120 or directly. As another example, the storage device 150 may be connected to the processing device 140 through the network 120 or directly.

The radiation delivery device 110 may be configured to deliver a radiotherapy treatment for cancers and other conditions. For example, the radiation delivery device 110 may deliver one or more radiation beams to a target area of a subject for causing an alleviation of the subject's symptom. The subject to be treated may include a biological subject (e.g., a human being, an animal, a plant, or a portion thereof) and/or a non-biological subject (e.g., a phantom). A target area refers to a certain anatomical structure that needs to be tracked or monitored during the radiotherapy treatment. For example, the target area may be a tumor, an organ with a tumor, a tissue with a tumor, or any combination thereof, that needs to be treated by radiation. In some embodiments, the radiation delivery device 110 may be a conformal radiation therapy device, e.g., an image-guided radiation therapy (IGRT) device, an intensity-modulated radiation therapy (IMRT) device, an intensity-modulated arc therapy (IMAT) device, an emission guided radiation therapy (EGRT), or the like.

In some embodiments, as illustrated in FIG. 1, the radiation delivery device 110 may include a gantry 111, a single treatment head 113, a beam control device 112, a table 114, and a control device (not shown in FIG. 1). The gantry 111 may be configured to support one or more components of the radiation delivery device 110, such as the treatment head 113 and/or the beam control device 112. The table 114 may be configured to support the subject during radiation treatment. The treatment head 113 may include, for example, a radiation beam generator configured to generate and emit a radiation beam (e.g., an X-ray beam) toward the subject. For example, the radiation beam may include electrons, photons, hadrons (e.g., protons, ions), or other types of radiation particles. The following descriptions are provided with reference to a radiation beam including electrons. It is understood that it is for illustration purposes and not intended to be limiting.

In some embodiments, the radiation beam generator may include a linear accelerator (also referred to as "Linac") configured to accelerate electrons to form an electron beam with a certain energy level. For example, the electrons may be accelerated to form an electron beam with a high energy level. As used herein, an electron beam with a high energy level refers to an electron beam with an energy greater than a threshold energy. The threshold energy may be, such as, 30 MeV, 40 MeV, 50 MeV, 100 MeV, 200 MeV, etc. An electron beam with an energy lower than the threshold energy may be referred to as an electron beam with a low energy level.

The beam control device 112 may be configured to modulate the radiation beam generated by the radiation beam generator. For example, the radiation beam generated by the radiation beam generator may be defocused, focused, and/or shaped by the beam control device 112, and enter the subject. In some embodiments, the beam control device 112 may modulate the radiation beam to achieve a desired depth dose distribution in the subject. As used herein, a depth refers to a distance with respect to the body surface of the subject measured in a direction parallel to a radiation beam that enters the subject (e.g., a central axis of the radiation beam). A depth dose distribution refers to a distribution of radiation dose at different depths. A desired depth dose distribution may be achieved if a larger portion of the total radiation dose is deposited in the target area than in the non-target area.

In some embodiments, the beam control device 112 may be mounted on the treatment head 113 or integrated into the treatment head 113. The gantry 111 may be rotatable, and the treatment head 113 and the beam control device 112 may rotate with the gantry 111. For example, the gantry 111 may rotate around a Y-axis on an X-Z plane defined by a coordinate system 160 as shown in FIG. 1. In some embodiments, the radiation delivery device 110 may include a plurality of treatment heads, each of which may be equipped with a beam control device 112. A beam control device 112 may be mounted on or integrated into the corresponding treatment head. In some embodiments, the radiation beam generator and the beam control device 112 may be an integral assembly.

Figure 4:
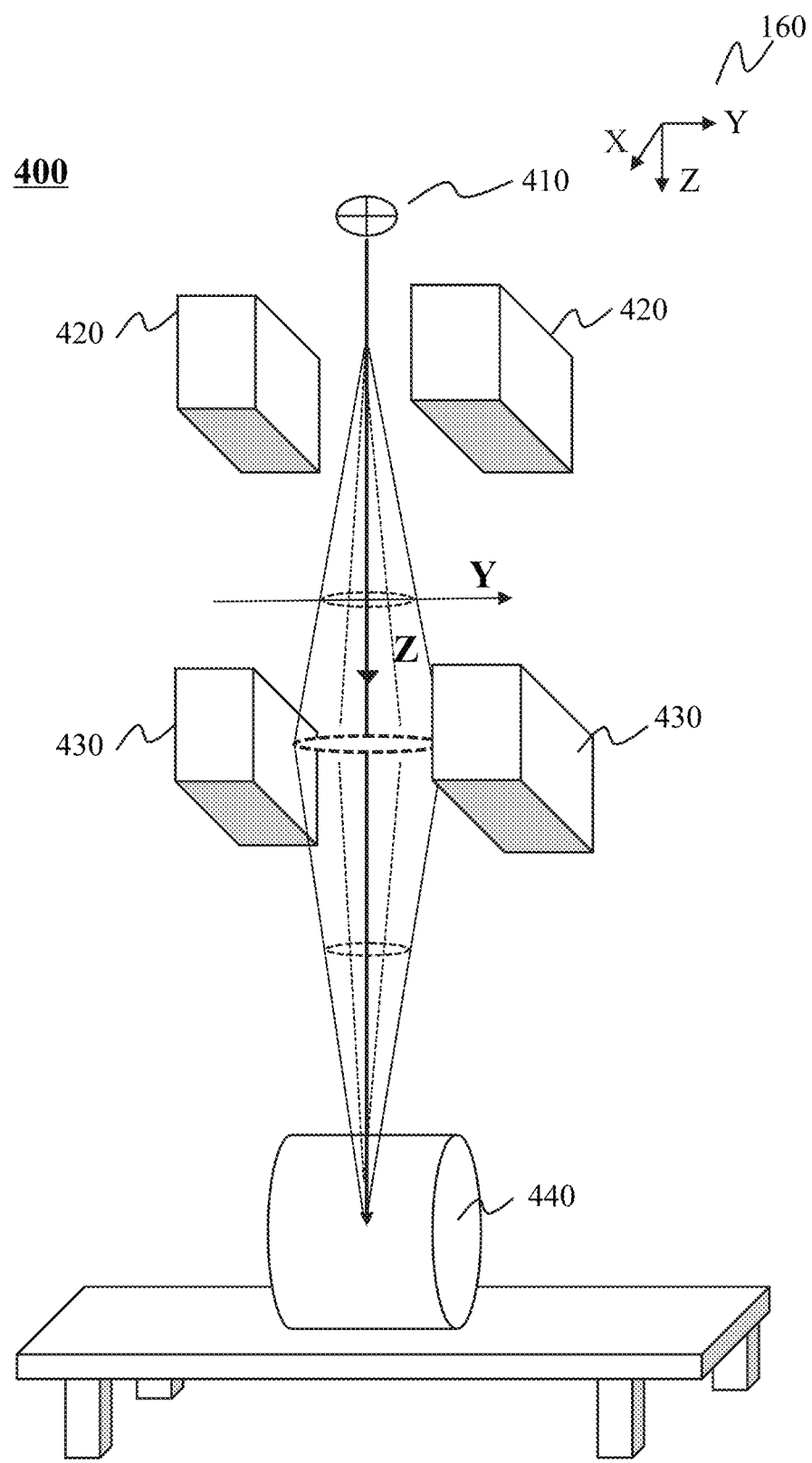
FIG. 4 is a schematic diagram illustrating an exemplary beam control device according to some embodiments of the present disclosure.

In some embodiments, the beam control device 112 may include a deflection device and/or a beam profile modulator. The deflection device may be configured to deflect the radiation beam. Merely by way of example, the radiation beam generator may emit an electron beam toward a direction (e.g., toward the subject), which may pass through the deflection device before reaching the subject. The moving trajectory (e.g., the moving direction) of the electron beam may be altered by the deflection device when it passes through the deflection device. Exemplary deflection devices may include a microwave cavity (e.g., a first microwave cavity 420, a second microwave cavity 430 as shown in FIG. 4), a magnet, a magnetic lens, or the like, or any combination thereof. More descriptions regarding a deflection device may be found elsewhere in the present disclosure. See, e.g., FIG. 4 and relevant descriptions thereof. The beam profile modulator may be configured to shape the radiation beam. Merely by way of example, the beam profile modulator may include one or more beam-limiting devices, such as a multi-leaf collimator, a blocker, that may block a specific portion of the radiation beam. More descriptions regarding a beam profile modulator may be found elsewhere in the present disclosure. See, e.g., FIGS. 6A and 6B and relevant descriptions thereof.

The control device may be configured to control one or more components of the radiation delivery device 110, such as the gantry 111, the radiation beam generator, and/or the beam control device 112. For example, the control device may be configured to determine one or more parameters of the beam control device 112 so as to optimize the depth dose distribution of the radiation beam in the subject. In some embodiments, the control device may be part of the radiation delivery device 110. In some alternative embodiments, the control device may be an independent device or part of another component of the RT system 100 (e.g., a terminal 130 or the processing device 140).

The network 120 may include any suitable network that can facilitate the exchange of information and/or data for the RT system 100. In some embodiments, one or more components of the RT system 100 (e.g., the radiation delivery device 110, the terminal(s) 130, the processing device 140, the storage device 150, etc.) may communicate information and/or data with one or more other components of the RT system 100 via the network 120. For example, the processing device 140 may transmit one or more parameters relating to the beam control device 112 to the radiation delivery device 110 via the network 120. As another example, the processing device 140 may obtain user instructions from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the RT system 100 may be connected to the network 120 to exchange data and/or information.

Figure 3:
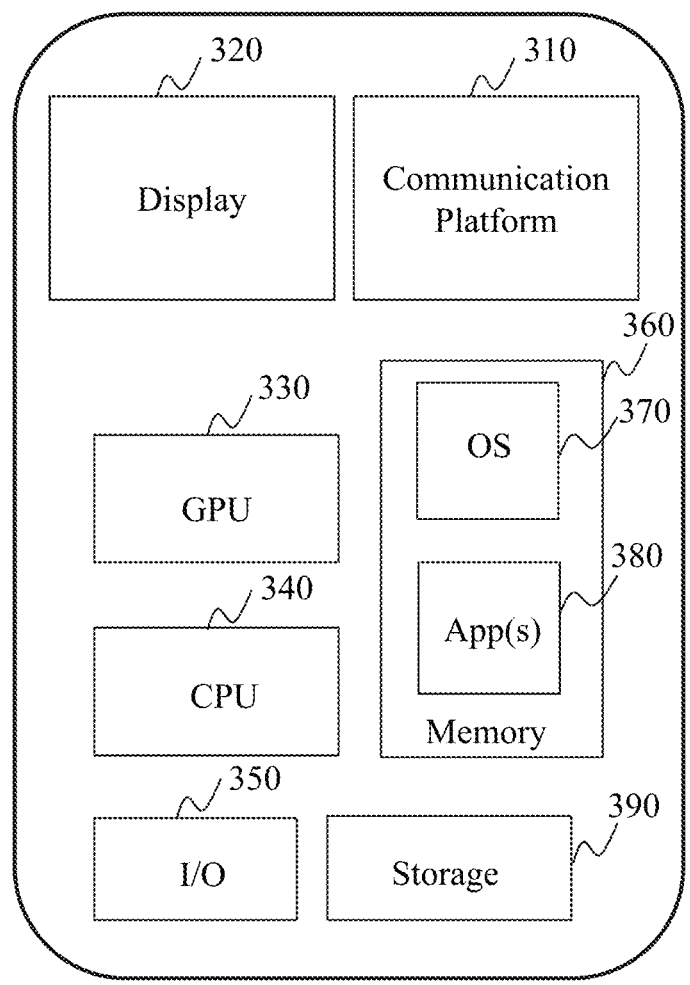
FIG. 3 is a schematic diagram illustrating exemplary hardware and/or software components of a mobile device according to some embodiments of the present disclosure.

The terminal(s) 130 may enable user interaction between a user and the RT system 100. In some embodiments, the terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal(s) 130 may include a mobile device as illustrated in FIG. 3.

In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footwear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140.

Figure 2:
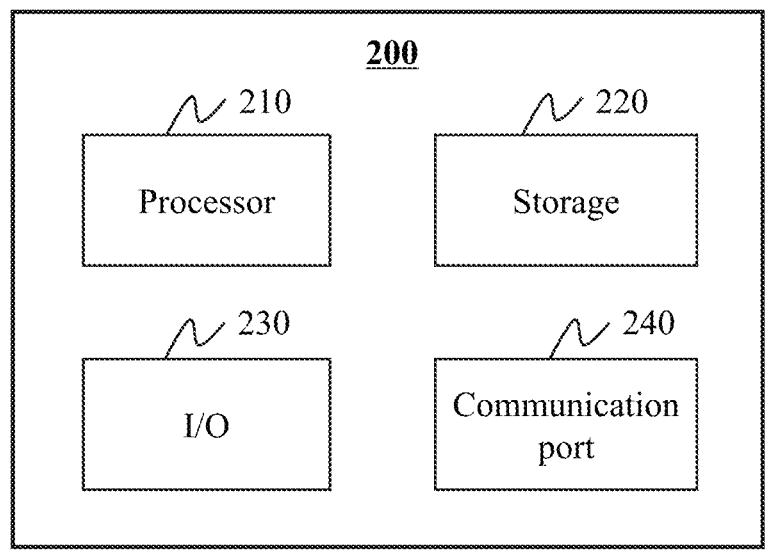
FIG. 2 is a schematic diagram illustrating exemplary hardware and/or software components of a computing device according to some embodiments of the present disclosure.

The processing device 140 may process information obtained from the radiation delivery device 110, the terminal(s) 130, and/or the storage device 150. For example, the processing device 140 may determine one or more parameters of the beam control device 112. In some embodiments, the control device of the radiation delivery device 110 as aforementioned may be implemented on the processing device 140. In some embodiments, the processing device 140 may be a computer, a user console, a single server, a server group, etc. The server group may be centralized or distributed. In some embodiments, the processing device 140 may be local or remote. For example, the processing device 140 may access information stored in the radiation delivery device 110, the terminal(s) 130, and/or the storage device 150 via the network 120. As another example, the processing device 140 may be directly connected to the radiation delivery device 110, the terminal(s) 130 and/or the storage device 150 to access stored information. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

The storage device 150 may store data, instructions, and/or any other information. In some embodiments, the storage device 150 may store data obtained from the terminal(s) 130 and/or the processing device 140. In some embodiments, the storage device 150 may store data and/or instructions that the control device of the radiation delivery device 110 and/or the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components of the RT system 100 (e.g., the radiation delivery device 110, the processing device 140, the terminal(s) 130). One or more components of the RT system 100 may access the data and/or instructions stored in the storage device 150 via the network 120. In some embodiments, the storage device 150 may be directly connected to or communicate with one or more other components of the RT system 100 (e.g., the processing device 140, the terminal(s) 130). In some embodiments, the storage device 150 may be part of the processing device 140. In some embodiments, the storage device 150 may be connected to or communicate with the radiation delivery device 110 via the network 120, or at the backend of the processing device 140.

For illustration purposes, a coordinate system 160 is provided in FIG. 1. As shown in FIG. 1, the coordinate system 160 may be an orthogonal coordinate system including an X-axis, a Y-axis, and a Z-axis. The Y-axis may be parallel to a rotation axis of the gantry 111. The X-axis and the X-axis may form a plane that is perpendicular to the Y-axis, wherein the X-axis may be horizontal and the Z-axis may be vertical. In some embodiments, the radiation delivery device 110 may include a plurality of treatment heads 113. The X-Z plane may be parallel to a plane where the plurality of treatment heads 113 are located, and the Y-axis may be perpendicular to the plane.

It should be noted that the above description regarding the RT system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the RT system 100 may include one or more additional components and/or one or more components of the RT system 100 described above may be omitted. Additionally or alternatively, two or more components of the RT system 100 may be integrated into a single component. A component of the RT system 100 may be implemented on two or more sub-components.

FIG. 2 is a schematic diagram illustrating exemplary hardware and/or software components of a computing device 200 according to some embodiments of the present disclosure. The computing device 200 may be used to implement any component of the RT system 100 as described herein. For example, the control device of the radiation delivery device 110, the processing device 140, and/or the terminal(s) 130 may be implemented on the computing device 200, respectively, via its hardware, software program, firmware, or a combination thereof. Although only one such computing device is shown, for convenience, the computer functions relating to the RT system 100 as described herein may be implemented in a distributed fashion on a number of similar platforms, to distribute the processing load. As illustrated in FIG. 2, the computing device 200 may include a processor 210, a storage 220, an input/output (I/O) 230, and a communication port 240.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process data obtained from the radiation delivery device 110, the terminal(s) 130, the storage device 150, and/or any other component of the RT system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method operations that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data obtained from one or more components of the RT system 100. In some embodiments, the storage 220 may include a mass storage device, a removable storage device, a volatile read-and-write memory, a read-only memory (ROM), or the like, or any combination thereof. In some embodiments, the storage 220 may store one or more programs and/or instructions to perform exemplary methods described in the present disclosure. For example, the storage 220 may store a program for the processing device 140 to execute to check errors in replanning.

The I/O 230 may input and/or output signals, data, information, etc. In some embodiments, the I/O 230 may enable user interaction with the computing device 200. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 140) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 120) to facilitate data communications. The communication port 240 may establish connections between the computing device and one or more other components. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee™ link, a mobile network link (e.g., 3G, 4G, 5G), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of a mobile device 300 according to some embodiments of the present disclosure. In some embodiments, a terminal(s) 130 and/or a processing device 140 may be implemented on a mobile device 300, respectively. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to the RT system 100. User interactions with the information stream may be achieved via the I/O 350 and provided to the processing device 140 and/or other components of the RT system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

FIG. 4 is a schematic diagram illustrating an exemplary beam control device 400 according to some embodiments of the present disclosure. The beam control device 400 may be configured to deliver an electron beam to a subject 440 (e.g., a patient or a portion thereof) and control the depth dose distribution of the electron beam in the subject 440. In some embodiments, the beam control device 400 may be an exemplary embodiment of the beam control device 112 as described in connection with FIG. 1. As illustrated in FIG. 4, the beam control device 400 may include an electron beam generator 410, a first microwave cavity 420, and a second microwave cavity 430.

The electron beam generator 410 may be configured to emit an electron beam for radiotherapy toward the subject 440 in a first direction. The first direction refers to an initial moving direction of the electron beam when the electron beam is generated. For example, the beam control device 400 may be mounted on a gantry that is rotatable on the X-Z plane around the Y-axis defined by the coordinate system 160 as shown in FIG. 4. The beam control device 400 may rotate with the gantry. The first direction may be associated with a gantry angle of the gantry. Merely by way of example, the electron beam generator 410 may be moved by the gantry to a location right above the subject 440 as shown in FIG. 4. The first direction may be parallel to the Z-axis. As another example, the beam control device 400 may be part of a certain treatment head of a radiation delivery device with a plurality of treatment heads. Each of the treatment heads may be located at a specific location and treat the subject 440 from a specific angle. The first direction may be associated with the position and/or the angle of the certain treatment head where the beam control device 400 is mounted.

In some embodiments, the electron beam may include a plurality of micro-bunches sequentially generated by the electron beam generator 410. A time interval between each pair of consecutive micro-bunches may have a fixed duration or a variable duration. For example, the time interval between each pair of consecutive micro-bunches may have a fixed duration. The fixed duration may be associated with the frequency of the electron beam generator 410. For example, the frequency of the electron beam generator 410 may be 2 GHz, and the time interval between each pair of adjacent micro-bunches may be 500 picoseconds (ps). As another example, the frequency of the electron beam generator 410 may be 3 GHz, and the time interval between each pair of adjacent micro-bunches may be 333 ps.

The electron beam may have a certain energy level. For example, the electron beam may have a high energy level, e.g., an energy greater than a threshold energy, such as 30 MeV, 40 MeV, 50 MeV, 100 MeV, 200 MeV, etc. Merely by way of example, the electron beam may have a high energy level in a range from 50 MeV to 300 MeV or 100 MeV to 300 MeV. As another example, the electron beam may have a low energy level, e.g., an energy lower than the threshold energy. In some embodiments, an electron beam with a high energy level may be referred to as a high-energy electron beam, and an electron beam with a low energy level may be referred to as a low-energy electron beam. The high-energy electron beam may have better penetrability than the low energy electron beam. The low energy electron beam may be more suitable for treating a target on or near the body surface of the subject, while the high-energy electron beam may be more suitable for treating a target inside the subject 440.

As shown in FIG. 4, the electron beam generated by the electron beam generator 410 may pass through a cavity (or channel) of the first microwave cavity 420. The first microwave cavity 420 may be configured to generate a defocused electron beam by defocusing the electron beam in a second direction. As used herein, the second direction may be any direction different from the first direction. The "defocusing a beam in a direction" refers to extending the range of the beam in the direction. For example, as shown in FIG. 4, the first direction may be parallel to the Z-axis, and the second direction may be parallel to the Y-axis (e.g., a rotation axis of a gantry where the beam control device 400 is mounted). After the electron beam passes through the first microwave cavity 420, the dimension of the electron beam in the Y-axis direction may be increased, i.e., the range of the electron beam in the Y-axis direction may be extended. If the electron beam generated by the electron beam generator 410 is regarded as a line along the Z-axis, a cross section of the defocused electron beam parallel to the X-Y plane may approximate a line extended along the Y-axis. It should be noted that the first microwave cavity 420 is provided as an example of a first deflection device configured to generate the defocused electron beam. The first microwave cavity 420 may be replaced by or used in combination with one or more other deflection devices, such as a defocusing magnet (e.g., a quadrupole defocusing magnet) and/or a defocusing lens, to achieve the defocusing of the electron beam.

In some embodiments, the first microwave cavity 420 may be configured to defocus the electron beam by applying a microwave field to the electron beam. For example, a microwave may be fed into the first microwave cavity 420, forming a microwave field within the first microwave cavity 420. When passing through the first microwave cavity 420, the electron beam may be deflected by a force in the second direction caused by the microwave field. In some embodiments, the microwave field in the first microwave cavity 420 may change over time (e.g., at a specific periodicity), which may result in a change of the force applied on the electron beam. For example, a direction and/or a magnitude of the microwave field may change, and a direction and/or a magnitude of the force applied on the electron beam may change with the change of the microwave field. Different micro-bunches of the electron beam passing through the first microwave cavity 420 at different times may be deflected by different forces in the second direction and have different moving trajectories after passing through the first microwave cavity 420. Merely by way of example, a first micro-bunch may be deflected in the positive Y-axis direction by a force in the positive Y-axis direction, and a second micro-bunch may be deflected in the negative Y-axis direction by a force in the negative Y-axis direction.

In some embodiments, one or more parameters of the first microwave cavity 420 may need to be adjusted such that the microwave field may defocus the electron beam in the second direction. Exemplary parameters of a microwave cavity may include a wavelength, a frequency, a phase, a direction, a magnitude, a periodicity, or the like, or any combination thereof, of the microwave field. In some embodiments, the microwave field may change at a periodicity. The periodicity of the microwave field may be greater than the time interval between each pair of adjacent micro-bunches of the electron beam. The frequency of the microwave field may be determined according to various factors, such as a frequency of the electron beam generator, a size of the first microwave cavity 420, etc. For example, if the frequency of the microwave field is low (e.g., lower than a threshold frequency), the wavelength of the microwave field may be long, and a larger first microwave cavity 420 may be needed. It may be desired that the first microwave cavity 420 generates a microwave field with a high frequency (e.g., higher than a threshold frequency) in order to reduce the equipment size. More descriptions regarding a microwave field of a microwave cavity may be found elsewhere in the present disclosure. See, e.g., FIGS. 7 to 9 and relevant descriptions thereof.

As illustrated in FIG. 4, the second microwave cavity 430 may be located between the first microwave cavity 420 and the subject 440. The second microwave cavity 430 may include a cavity (or channel), and the defocused electron beam may pass through the second microwave cavity 430 after leaving the first microwave cavity 420. The second microwave cavity 430 may be configured to generate a focused electron beam by focusing the defocused electron beam in the second direction. As used herein, the "focusing a beam in a direction" refers to narrowing the range of the beam in the direction. For example, as shown in FIG. 4, the first direction and the second direction may be parallel to the Z-axis and the Y-axis, respectively. After the defocused electron beam passes through the second microwave cavity 430, the dimension of the defocused electron beam in the Y-axis direction may be reduced, i.e., the range of the defocused electron beam in the Y-axis direction may be narrowed. It should be noted that the second microwave cavity 430 is provided as an example of a second deflection device configured to generate the focused electron beam. The second microwave cavity 430 may be replaced by or used in combination with one or more other deflection devices, such as a focusing magnet (e.g., a quadrupole focusing magnet), a focusing lens, to achieve the focusing of the defocused electron beam.

In some embodiments, the second microwave cavity 430 may be configured to focus the defocused electron beam by applying a second microwave field to the defocused electron beam. For example, a microwave may be fed into the second microwave cavity 430, forming a second microwave field within the second microwave cavity 430. When passing through the second microwave cavity 430, the defocused electron beam may be deflected by a force in the second direction caused by the second microwave field. In some embodiments, the intensity of the second microwave field in the second microwave cavity 430 may change over time (e.g., at a specific periodicity), which may result in a change of the force applied on the defocused electron beam. Different micro-bunches of the defocused electron beam passing through the second microwave cavity 430 at different times may be deflected by different forces in the second direction and have different moving trajectories after passing through the second microwave cavity 430.

In some embodiments, a micro-bunch of the electron beam may be deflected by a force F1 in the first microwave cavity 420 and a force F2 in the second microwave cavity 430, wherein the forces F1 and F2 may be in opposite directions. Merely by way of example, as aforementioned, in the first microwave cavity 420, the first micro-bunch and the second micro-bunch may be deflected by forces in the positive Y-axis direction and the negative Y-axis direction, respectively. In the second microwave cavity 430, the first micro-bunch may be deflected in the negative Y-axis direction by a force in the negative Y-axis direction, and the second micro-bunch may be deflected in the positive Y-axis direction by a force in the positive Y-axis direction. In some embodiments, one or more parameters of the second microwave cavity 430 may need to be adjusted such that the second microwave field may focus the defocused electron beam in the second direction. The parameter adjustment of the second microwave cavity 430 may be performed in a similar manner with that of the first microwave cavity 420, and the descriptions thereof are not repeated here.

In some embodiments, the first microwave cavity 420 and/or the second microwave cavity 430 may be controlled by a control device of the beam control device 400. The control device may be part of a radiation delivery device where the beam control device 400 is mounted. Alternatively, the control device may be a device independent from the radiation delivery device, for example, implemented on the processing device 140 or a terminal 130 as described in connection with FIG. 1.

For example, the control device may determine one or more parameters of the first microwave cavity 420 and the second microwave cavity 430 such that the focused electron beam is focused on a target area (e.g., a tumor) of the subject 440 in the second direction. Merely by way of example, it is assumed that the second direction is the Y-axis direction. If the target area of the subject 440 corresponds to a specific coordinate range in the Y-axis, the Y-coordinate of the focal spot of the focused electron beam may be adjusted to the specific range by the second microwave cavity 430. In such cases, the focused electron beam may be regarded as being focused on the target area in the Y-axis direction. In some embodiments, the parameter(s) of the first microwave cavity 420 and the second microwave cavity 430 may be determined based on, for example, a planned dose distribution, a position of the electron beam generator 410 relative to the target area, a position of the first microwave cavity 420 relative to the target area, a position of the second microwave cavity 430 relative to the target area, or the like, or any combination thereof.

As aforementioned, in some embodiments, the electron beam may be defocused and focused in a certain direction (e.g., the second direction) before entering the subject 440. The focused electron beam may be focused on the target area, thereby depositing more radiation dose on the target area and forming a "Bragg peak" like a hadron beam. Before reaching the target area, the focused electron beam may have a greater irradiation area in the subject 440, while the original electron beam may have a relatively small irradiation area if it is not defocused and focused. In other words, the radiation dose of the defocused electron beam may be scattered in the non-target area (e.g., the body surface and/or health organs between the body surface and the target area of the subject) more widely than the original electron beam, which may avoid or reduce a dose deposition in the non-target area. In this way, a desired depth dose distribution may be achieved, thereby improving the precision of treatment delivery, and/or reducing or avoiding unnecessary damages to the subject caused by unintended radiation.

In addition, the deflection of the electron beam may be implemented by a pair of the first microwave cavity 420 and the second microwave cavity 430 according to some embodiments of the present disclosure. Compared with a deflection device (e.g., a magnet or a magnetic lens) that provides a constant deflection force, a microwave cavity may provide a dynamic microwave field and have higher energy efficiency. Moreover, the microwave field of a microwave cavity may have a higher field gradient than a magnetic field of a magnet. If the microwave field applies a same force on electrons as the magnetic field, it may achieve a better defocusing and/or focusing effect on electrons than the magnet field.

Furthermore, by using the beam control device 400 (or a portion thereof), the radiation delivery device may treat the subject 440 from more angles and the flexibility of the radiation delivery device 110 may be improved. For example, the gantry of the radiation delivery device may rotate on the X-Z plane as shown in FIG. 4. The orientation of the electron beam on the X-Z plane may be adjusted via gantry rotation. The orientation of the electron beam on the Y-axis may be adjusted via the beam control device 400. As another example, the radiation delivery device may include a plurality of treatment heads each of which may be located at a specific location and treat the subject from a specific angle. Each treatment head may be equipped with a beam control device 400 (or a portion thereof) for expending the angle of the treatment head. Merely by way of example, a treatment head may be located at a same position as the electron beam generator 410 and configured to emit an electron beam along a positive Z-axis direction. A microwave cavity like the first microwave cavity 420 may be mounted on the treatment head to defocus the electron beam in the X-axis direction. In this way, the treatment head may treat a target area of the subject with a wider range of angles, e.g., within ±10° with respect to the positive Z-axis.

It should be noted that the beam control device 400 in FIG. 4 and the descriptions thereof are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure.

The shape, the size, and/or the position of a component of the beam control device 400 shown in FIG. 4 are illustrative and not intended to be limiting. Merely by way of example, the first microwave cavity 420 and its cavity may have any suitable shape and/or size. In addition, the first, second, and third directions as indicated in FIG. 4 are provided for illustration purposes and may be modified according to actual needs. Merely by way of example, the second direction may be parallel to the X-axis and the third direction may be parallel to the Y-axis.

In some embodiments, the beam control device 400 may include one or more additional components. For example, the beam control device 400 may include a beam profile modulator (e.g., the beam profile modulator 610) for beam shaping and/or a scanning electrode (e.g., the scanning electrode 510). As another example, the beam control device 400 may include one or more deflection devices for deflecting the focused electron beam in a third direction. The third direction may be any direction different from each of the first direction and the second direction. Merely by way of example, the first and second directions may be the Z-axis direction and the Y-axis direction, respectively. The third direction may be the X-axis direction.

In some embodiments, the additional deflection devices may include a defocusing component and a focusing component. After leaving the second microwave cavity 430, the focused electron beam may pass through the defocusing component, which may be configured to generate a second defocused electron beam by defocusing the focused electron beam in the third direction. The second defocused electron beam may pass through the focusing component after leaving the defocused component, and the focusing component may be configured to generate a second focused electron beam by focusing the second defocused electron beam in the third direction. The second focused electron beam may then enter the subject 440. In some embodiments, one or more parameters of the defocusing component and the focusing component may be adjusted, for example, by the control device, such that the second focused electron beam may focus on the target area in the third direction.

Exemplary defocusing components may include a third microwave cavity, a defocusing magnet (e.g., a quadrupole defocusing magnet), a defocusing lens, or the like, or any combination thereof. The third microwave cavity may have a same or similar structure as the first microwave cavity 420. Exemplary focusing components may include a fourth microwave cavity, a focusing magnet (e.g., a quadrupole focusing magnet), a focusing lens, or the like, or any combination thereof. The fourth microwave cavity may have a same or similar structure as the first microwave cavity 420.

In some embodiments, one or more components of the beam control device 400 described above may be omitted. For example, the second microwave cavity 430 may be omitted. Additionally or alternatively, a component of the beam control device 400 may be replaced by another component that can implement the same or similar functions. For example, the first microwave cavity 420 may be replaced by another deflection device, such as a defocusing magnet, a defocusing lens, or the like.

In some embodiments, a microwave cavity may be replaced by another device that can apply a force on an electron beam to defocus or focus the electron beam. Merely by way of example, a device may generate a laser field instead of a microwave field to defocus or focus the electron beam. For illustration purposes, the term "microwave cavity" is used herein to collectively refer to devices capable of applying a force on the electron beam to defocus or focus the electron beam, and the term "microwave field" is used herein to collectively refer to a field applied by such devices.

Figure 5:
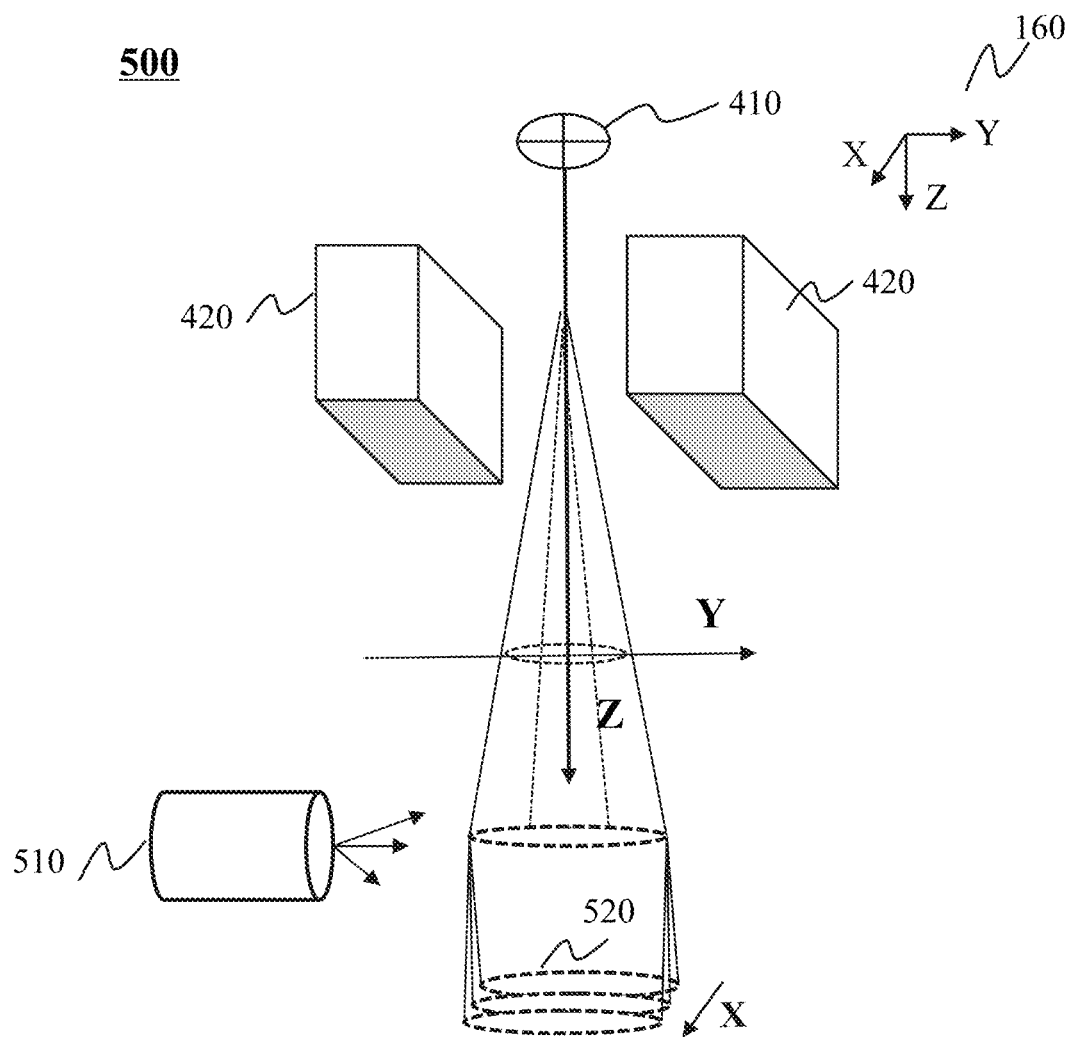
FIG. 5 is a schematic diagram illustrating an exemplary beam control device according to some embodiments of the present disclosure.

FIG. 5 is a schematic diagram illustrating an exemplary beam control device 500 according to some embodiments of the present disclosure. In some embodiments, the beam control device 500 may be an exemplary embodiment of the beam control device 112 as described in connection with FIG. 1.

As illustrated in FIG. 5, the beam control device 500 may be similar to the beam control device 400 as described in connection with FIG. 4, except that the beam control device 500 may include a scanning electrode 510, instead of the second microwave cavity 430. The scanning electrode 510 may be located between the first microwave cavity 420 and a subject to be scanned (not shown in FIG. 5).

The scanning electrode 510 may be configured to scan the defocused electron beam from a fourth direction. The fourth direction may be any direction different from each of the first direction and the second direction. The first direction may be the same as or different from the third direction. For example, as illustrated in FIG. 1, the first direction and the second direction may be the Z-axis direction, and the Y-axis direction, respectively. The fourth direction may be the X-axis direction. During the scan of the defocused electron beam, the scanning electrode 510 may apply an electric field on the defocused electron beam. The intensity and/or direction of the electric field may change over time such that different micro-bunches of the defocused electron beam may be deflected by different forces in the fourth direction.

For the convenience of descriptions, the defocused electron beam after scanning is referred to as a target electron beam. In some embodiments, a cross section of the target electron beam may include a plurality of strips or lines, which are spaced apart from each other along the fourth direction. Merely by way of example, as shown in FIG. 5, the electron beam generator 410 may emit an electron beam in the Z-axis direction, and the first microwave cavity 420 may defocus the electron beam in the Y-axis direction. The scanning electrode 510 may scan the defocused electron beam in the X-axis direction, thereby generating a target electron beam. A certain cross section of the target electron beam parallel to the X-Y plane may include a plurality of strips 520. The strips 520 may be regarded as a plurality of parallel lines with a same length evenly or unevenly distributed along the X-axis direction.

In some embodiments, adjacent strips of the strips 520 may be close to each other (e.g., with a distance shorter than a threshold distance) such that the strips 520 may approximately form a treatment plane on the certain cross section. Such target electron beam may be utilized to treat a certain area in a plane in the subject, which may have a higher treatment efficiency than an electron beam focused on a single spot. In some embodiments, the beam control device 500 may include one or more additional deflection devices, such as another microwave cavity, a focusing lens, or the like. For example, a fourth microwave cavity may be mounted between the scanning electrode 510 and the subject. The fourth microwave cavity may be configured to focus and/or defocus the target electron beam in the second direction (or another direction) to control the lengths (in the second direction) of the strips 520. Merely by way of example, different microwave fields may be applied to micro-bunches of different strips such that the strips may have different lengths along the second direction.

It should be noted that the above descriptions of the beam control device 500 are provided for the purposes of illustration, and not intended to limit the scope of the present disclosure. For persons having ordinary skills in the art, various modifications and changes in the forms and details of the application of the above method and system may occur without departing from the principles of the present disclosure. However, those variations and modifications also fall within the scope of the present disclosure. In some embodiments, the beam control device 500 may include one or more other components and/or one or more components described above may be omitted. Additionally or alternatively, a component of the beam control device 500 may be replaced by another component that can implement same or similar functions. In addition, the first, second, and fourth directions as indicated in FIG. 5 are provided for illustration purposes and may be modified according to actual needs.

Figure 6A:
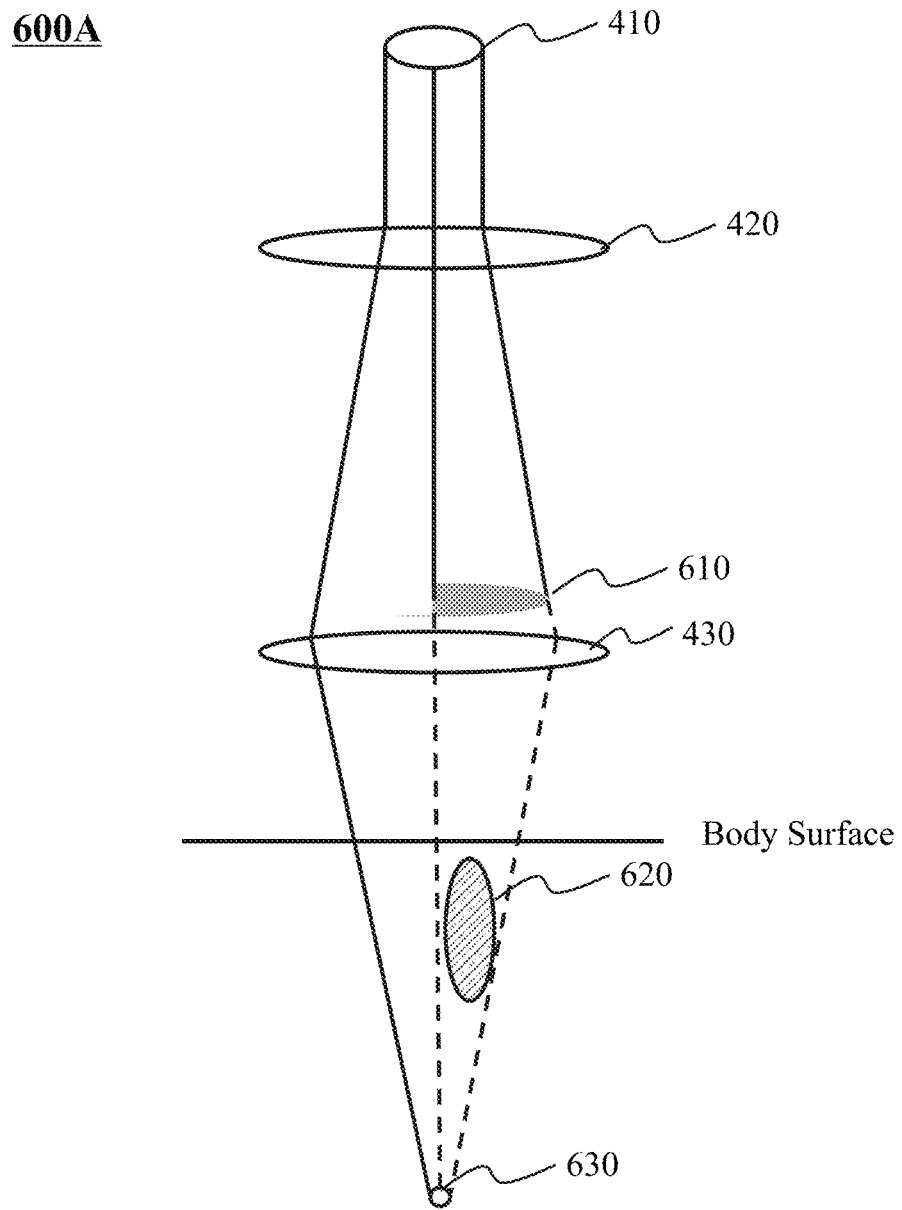
FIG. 6A is a schematic diagram illustrating an exemplary beam control device according to some embodiments of the present disclosure.

FIG. 6A is a schematic diagram illustrating an exemplary beam control device 600A according to some embodiments of the present disclosure. As illustrated in FIG. 6A, the beam control device 600A may be configured to control an electron beam delivered to a subject. The subject may include a target area 630 (e.g., a tumor) and a non-target area 620. The beam control device 600A may be similar to the beam control device 400 as described in connection with FIG. 4, except that the beam control device 600A may further include a beam profile modulator 610.

The beam profile modulator 610 may be located between the first microwave cavity 420 and the second microwave cavity 430 and configured to shape the defocused electron beam. For example, the beam profile modulator 610 may include one or more beam-limiting devices, such as a multi-leaf collimator, a blocker, that may block a specific portion of the defocused electron beam. The specific portion of the defocused electron beam may cause dose disposition in the non-target area 620 if it is not blocked. Merely by way of example, as shown in FIG. 6A, the right half of the defocused electron beam may be blocked by the beam profile modulator 610, thereby avoiding a dose deposition in the non-target area 620. In some embodiments, the shape of the beam profile modulator 610 may be adjusted such that the remaining portion of the electron beam may have a better conformity to the target area 630.

Figure 6B:
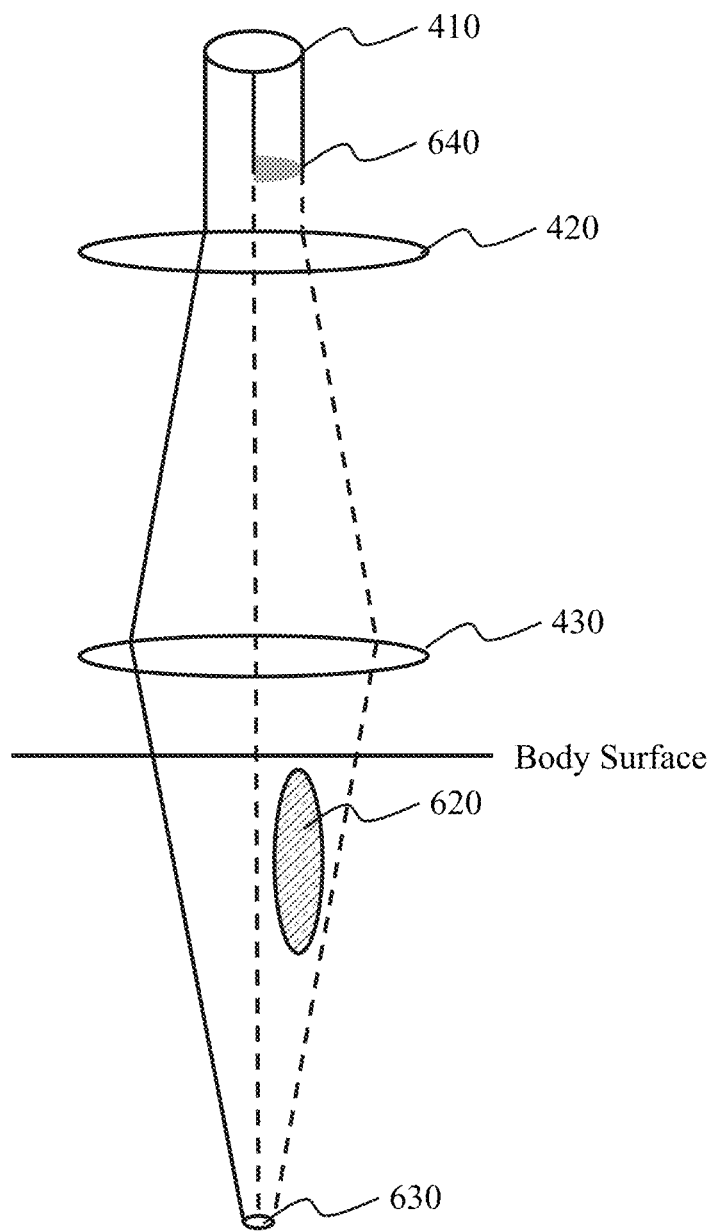
FIG. 6B is a schematic diagram illustrating an exemplary beam control device according to some embodiments of the present disclosure.

FIG. 6B is a schematic diagram illustrating an exemplary beam control device 600B according to some embodiments of the present disclosure. The beam control device 600B may be similar to the beam control device 600A as described in connection with FIG. 6A, except that the beam control device 600B may include a beam profile modulator 640 instead of the beam profile modulator 610. The beam profile modulator 640 may be located between the electron beam generator 410 and the first microwave cavity 420 and configured to shape the electron beam generated by the electron beam generator 410. In some embodiments, a beam profile modulator located at different positions along the transmission path of the electron beam may have different configurations (e.g., shapes and/or sizes). Merely by way of example, the electron beam may have a relatively smaller size before it is defocused by the first microwave cavity 420. The beam profile modulator 610 for shaping the defocused electron beam may have a greater size than the beam profile modulator 640 for shaping the electron beam.

It should be noted that the above descriptions of the beam control device 600A and 600B are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the beam control device 600A or 600B may include one or more other components and/or one or more components described above may be omitted. For example, the beam control device 600A or 600B may include a plurality of beam profile modulators. Additionally or alternatively, a component of the beam control device 600A or 600B may be replaced by another component that can implement same or similar functions. For example, the first microwave cavity 420 may be replaced by a defocusing lens, and/or the second microwave cavity 430 may be replaced by a focusing lens.

Figure 7:
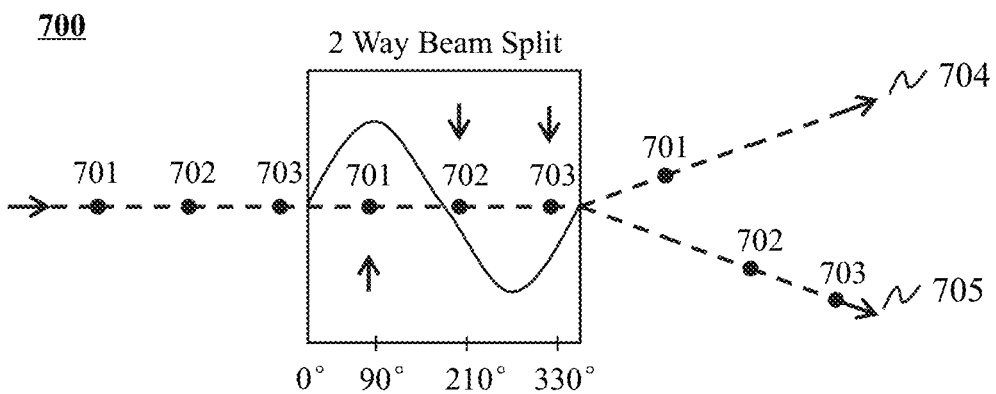
FIG. 7 illustrates an exemplary waveform of a microwave field according to some embodiments of the present disclosure.

FIG. 7 illustrates an exemplary waveform of a microwave field 700 according to some embodiments of the present disclosure. The microwave field 700 may be generated by a microwave cavity (e.g., the first microwave cavity 420, the second microwave cavity 430) as described elsewhere in this disclosure (e.g., FIG. 4 and the relevant descriptions). The intensity of the microwave field 700 may change periodically with a periodicity T. The dark spots in FIG. 7 may represent a plurality of micro-bunches (e.g., 701, 702, and 703) of an electron beam (e.g., the electron beam generated by the electron beam generator 410 or the defocused electron beam as described in connection with FIG. 4).

The micro-bunches may sequentially pass through the microwave cavity with a time interval T/3 between each pair of consecutive micro-bunches. Each of the micro-bunches 701 may be deflected by a force F1 corresponding to a positive phase 90° of the microwave field 700. Each of the micro-bunches 702 may be deflected by a force F2 corresponding to a negative phase 210° of the microwave field 700. Each of the micro-bunches 703 may be deflected by a force F3 corresponding to a negative phase 330° of the microwave field 700. The force F1 may have an opposite direction to the force F2 and the force F3. The force F2 and the force F3 may have the same magnitude and be in the same direction. After passing through the first microwave cavity, each of the micro-bunches 701 may move along a direction as indicated by an arrow 704 as shown in FIG. 7, while each of the micro-bunches 702 and 703 may move along a direction as indicated by an arrow 705 as shown in FIG. 7. The electron beam may be split into two portions.

Figure 8:
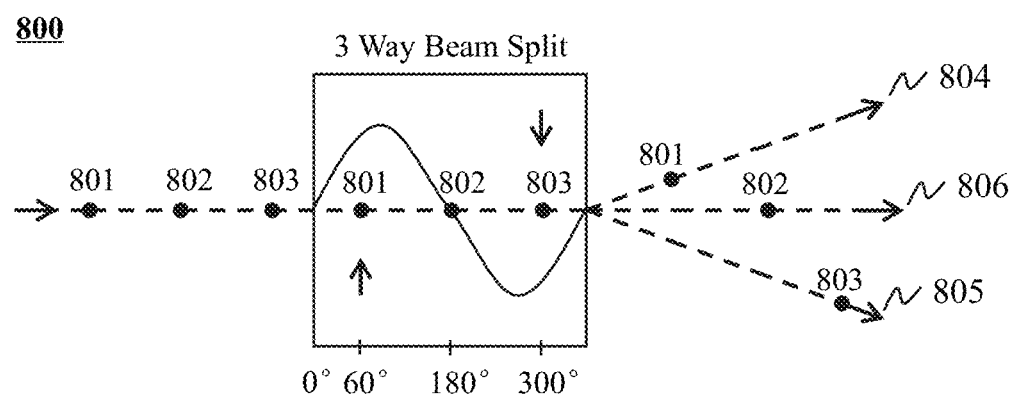
FIG. 8 illustrates an exemplary waveform of a microwave field according to some embodiments of the present disclosure.

FIG. 8 illustrates an exemplary waveform of a microwave field 800 according to some embodiments of the present disclosure. The microwave field 800 may be similar to the microwave field 700 as described in connection with FIG. 7. The dark spots in FIG. 8 may represent a plurality of micro-bunches (e.g., 801, 802, and 803) of an electron beam (e.g., the electron beam generated by the electron beam generator 410 or the defocused electron beam as described in connection with FIG. 4).

The micro-bunches may sequentially pass through the microwave cavity with a time interval T/3 between each pair of consecutive micro-bunches. Each of the micro-bunches 801 may be deflected by a force F1' corresponding to a positive phase 60° of the microwave field 800. Each of the micro-bunches 802 may be deflected by a force F2' corresponding to a zero phase 180° of the microwave field 800. Each of the micro-bunches 803 may be deflected by a force F3' corresponding to a negative phase 300° of the microwave field 800. The force F1' may have an opposite direction to the force F3. The magnitude of the force F2' may be 0, that is, no force may be applied to the micro-bunches 802. After passing through the microwave cavity, each of the micro-bunches 801 may move along a direction as indicated by an arrow 804 as shown in FIG. 8, each of the micro-bunches 802 may move along a direction as indicated by an arrow 806 as shown in FIG. 8, and each of the micro-bunches 803 may move along a direction as indicated by an arrow 805 as shown in FIG. 8. The electron beam may be split into three portions.

In some embodiments, the microwave field 700 or microwave field 800 may be generated by the first microwave cavity 420. The forces F1, F2, F3, F1', F2', and F3' may be in the second direction. For example, the force F1 may be in the positive Y-axis direction. The forces F2 and F3 may be both in the negative Y-axis direction.

Figure 9:
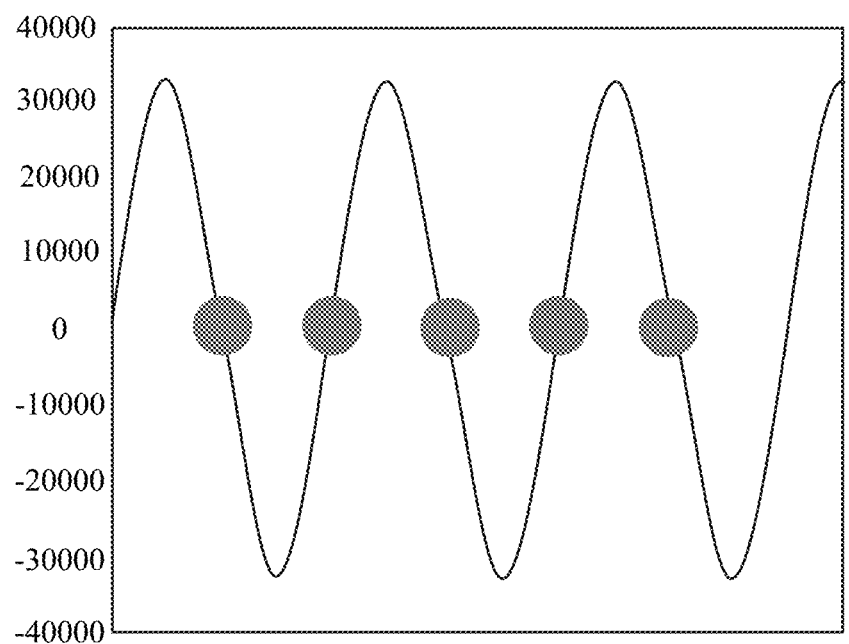
FIG. 9 illustrates an exemplary waveform of a microwave field according to some embodiments of the present disclosure.

FIG. 9 illustrates an exemplary waveform of a microwave field 900 according to some embodiments of the present disclosure. The horizontal axis and the vertical axis in FIG. 9 may represent the time and the intensity of the microwave field 900, respectively. The microwave field 900 may be generated by a microwave cavity (e.g., the first microwave cavity 420) as described elsewhere in this disclosure (e.g., FIG. 4 and the relevant descriptions). The intensity of the microwave field 900 may change periodically with a periodicity T'.

The grey spots in FIG. 9 may represent a plurality of micro-bunches of an electron beam (e.g., the electron beam generated by the electron beam generator 410). The micro-bunches may sequentially pass through the microwave cavity with a time interval T'/2 between each pair of consecutive micro-bunches. No force may be applied to the center of each of the micro-bunches. Because each micro-bunch may have a certain length, the other part of each micro-bunch (e.g., two ends of each micro-bunch) may be deflected by a force caused by the microwave field 900. In this way, the electron beam may be defocused to some extent.

It should be noted that the examples illustrated in FIGS. 7 to 9 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the time interval between each pair of consecutive micro-bunches of an electron beam and/or the frequency of a microwave field may be adjusted according to an actual need.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A beam control device for radiotherapy, comprising:
an electron beam generator configured to emit an electron beam for radiotherapy toward a subject in a first direction; and
a first deflection device configured to generate a defocused electron beam by defocusing the electron beam in a second direction, the second direction being different from the first direction, wherein the first deflection device includes at least one of a first microwave cavity, a device configured to generate a laser field to defocus the electron beam, or a lens.

2. The beam control device of claim 1, wherein an energy of the electron beam is in a range from 50 megaelectron volts (MeV) to 300 MeV.

3. The beam control device of claim 1, wherein the electron beam generator is mounted on a gantry, and the second direction is parallel to a rotation axis of the gantry.

4. The beam control device of claim 1, wherein the first deflection device includes the first microwave cavity.

5. The beam control device of claim 4, further comprising:
a second deflection device configured to generate a focused electron beam by focusing the defocused electron beam.

6. The beam control device of claim 5, wherein the second deflection device includes a second microwave cavity.

7. The beam control device of claim 6, further comprising:
a defocusing component configured to generate a second defocused electron beam by defocusing the focused electron beam in a third direction, the third direction being different from each of the first direction and the second direction; and
a focusing component configured to generate a second focused electron beam by focusing the second defocused electron beam in the third direction.

8. The beam control device of claim 7, wherein the electron beam generator is mounted on a gantry, and the third direction is a horizontal direction perpendicular to a rotation axis of the gantry.

9. The beam control device of claim 7, wherein at least one of the defocusing component or the focusing component comprises at least one of a microwave cavity, a device configured to generate a laser field to defocus the electron beam, a lens, a magnet, or a magnetic lens.

10. The beam control device of claim 6, further comprising:
a control device configured to control the first microwave cavity and the second microwave cavity such that the focused electron beam is focused on a target area of the subject in the second direction.

11. The beam control device of claim 10, wherein to control the first microwave cavity and the second microwave cavity, the control device is configured to:
  determine one or more parameters of the first microwave cavity and the second microwave cavity based on at least one of a planned dose distribution, a position of the electron beam generator relative to the target area, a position of the first microwave cavity relative to the target area, or a position of the second microwave cavity relative to the target area.

12. The beam control device of claim 4, further comprising a beam profile modulator, wherein
  the beam profile modulator is placed between the electron beam generator and the first microwave cavity and configured to shape the electron beam generated by the electron beam generator, and
  the first microwave cavity is configured to defocus the shaped electron beam.

13. The beam control device of claim 12, wherein the beam profile modulator comprises at least one of a multi-leaf collimator or a blocker.

14. The beam control device of claim 4, further comprising a second beam profile modulator configured to shape the defocused electron beam, wherein the first microwave cavity is placed between the electron beam generator and the second beam profile modulator.

15. The beam control device of claim 4, wherein the first microwave cavity is configured to defocus the electron beam in the second direction by applying a microwave field to the electron beam, the microwave field changing over time.

16. The beam control device of claim 15, wherein
  the electron beam includes a plurality of micro-bunches sequentially generated by the electron beam generator with a time interval between each pair of consecutive micro-bunches of the plurality of micro-bunches,
  the microwave field changes at a periodicity, and
  the periodicity of the microwave field is longer than the time interval.

17. The beam control device of claim 1, further comprising:
  a scanning electrode configured to scan the defocused electron beam in a direction different from each of the first direction and the second direction.

18. A radiation delivery device, comprising:
  at least one treatment head, which comprises a beam control device according to claim 1.

19. The system of claim 18, wherein the radiation delivery device comprises a plurality of treatment heads, and each of the plurality of treatment heads includes the beam control device.

20. The beam control device of claim 19, wherein the second direction is perpendicular to a plane where the plurality of treatment heads are located.

* * * * *